(12) United States Patent
Ouyang

(10) Patent No.: US 10,548,865 B1
(45) Date of Patent: Feb. 4, 2020

(54) COMPOSITIONS OF CITRULLINE

(71) Applicant: Hubei Grand Biotechnology Co. Ltd., Huangshi (CN)

(72) Inventor: Hui Ouyang, Hubei (CN)

(73) Assignee: Hubei Grand Biotechnology Co. Ltd., Huangshi (CN)

( * ) Notice: Subject to any disclaimer, the term of this patent is extended or adjusted under 35 U.S.C. 154(b) by 0 days.

(21) Appl. No.: 16/374,625

(22) Filed: Apr. 3, 2019

Related U.S. Application Data

(63) Continuation of application No. PCT/CN2019/078623, filed on Mar. 19, 2019.

(51) Int. Cl.
| | |
|---|---|
| *A61K 31/198* | (2006.01) |
| *A61K 31/185* | (2006.01) |
| *A61K 9/00* | (2006.01) |
| *A61P 21/00* | (2006.01) |
| *A23L 2/52* | (2006.01) |
| *A23L 33/175* | (2016.01) |
| *A23L 33/16* | (2016.01) |
| *A61P 21/06* | (2006.01) |

(52) U.S. Cl.
CPC .............. *A61K 31/198* (2013.01); *A23L 2/52* (2013.01); *A23L 33/16* (2016.08); *A23L 33/175* (2016.08); *A61K 9/0095* (2013.01); *A61K 31/185* (2013.01); *A61P 21/00* (2018.01); *A61P 21/06* (2018.01); *A23V 2002/00* (2013.01)

(58) Field of Classification Search
CPC .. A61K 31/198; A61K 9/0095; A61K 31/185; A23L 33/175; A23L 33/16; A23L 2/52; A61P 21/00; A61P 21/06; A23V 2002/00
See application file for complete search history.

(56) References Cited

U.S. PATENT DOCUMENTS 8,642,095 B2 * 2/2014 Sommerfeld ............. A23L 2/38
424/725

OTHER PUBLICATIONS

Jagim et al. Common Ingredient Profiles of Multi-Ingredient Pre-Workout Supplements. Nutrients (epub. Jan. 2019), 11, 254, 8 pages. (Year: 2019).*
PubChem ID entry 1123—Taurine, 135 pages; created 2004 (Year: 2004).*
PubChem ID entry 9750—Citrulline, 73 pages, created 2004 (Year: 2004).*

* cited by examiner

*Primary Examiner* — Sean C. Barron
(74) *Attorney, Agent, or Firm* — Sheppard Mullin Richter & Hampton LLP

(57) ABSTRACT

The present disclosure relates generally to supplement compositions containing citrulline and taurine at a weight ratio of 4.56:1 to 2.57:1 which have been demonstrated to have a pleasant flavor and can enhance the exercise endurance in individuals in a synergistic manner.

18 Claims, 3 Drawing Sheets

COMPOSITIONS OF CITRULLINE

CROSS REFERENCE TO RELATED APPLICATION

The present application is a continuation application of International Application PCT/CN2019/078623, filed Mar. 19, 2019, the contents of which are incorporated by reference in their entireties into the present disclosure.

BACKGROUND

L-citrulline, or simply citrulline, is an α-amino acid, with its name derived from citrullus, the Latin word for watermelon. Citrulline is a key intermediate in the urea cycle, the pathway by which mammals excrete ammonia by converting it into urea. Citrulline is also produced as a byproduct of the enzymatic production of nitric oxide from the amino acid arginine, catalyzed by nitric oxide synthase.

Citrulline boosts nitric oxide (NO) production in the body. Nitric oxide helps arteries relax and work better, which improves blood flow throughout the body. NO is an integral part of the inflammatory phase, functioning as a regulatory mechanism to mediate epithelialization, angiogenesis, and collagen deposition crucial to the proliferative phase. NO-induced vasodilatation acted as a host-protective agent by killing pathogens and by increasing blood flow to wounds. The supplement of citrulline is used to lower blood pressure in people with prehypertension. Citrulline supplements may also ease symptoms of mild-to-moderate erectile dysfunction (ED) and help to address blood vessel problems such as slow wound healing due to diabetes.

Bodybuilders use citrulline malate, a formulation of L-citrulline with malic acid added, as a supplement. It is hypothesized that citrulline malate can increase NO and growth hormone synthesis, and can therefore promote improvements in athletic performance and physical energy levels. Such performance enhancement effects of citrulline, however, lack clinical validation.

SUMMARY

The present disclosure, in certain embodiments, provides solid compositions and drinks that contain citrulline and taurine. As the accompanying experimental examples show, citrulline was able to enhance the physical performance of mice, and the addition of taurine significantly and synergistically boosted the enhancement even further. By contrast, gamma-aminobutyric acid (GABA), which would have been thought to be more likely to synergize with citrulline, did not even produce additive effects.

Also, even though taurine has a strong unpleasant astringent bitter taste in solutions, when it was added to citrulline, it unexpectedly improved the tastes of citrulline which on its own only has a mild unnatural taste in solutions. When more taurine was added (e.g., when there was more taurine than citrulline in the solution) its astringent bitter taste overshadows the milder taste of citrulline. Taurine's ability to improve the taste of citrulline in solutions, at suitable weight ratios is another surprising discovery of the present disclosure.

In one embodiment, therefore, the present disclosure provides a composition comprising citrulline and taurine. In some embodiments, the citrulline and the taurine have a weight ratio of 5:1 to 1:5, or 5:1 to 1:1, or 4.56:1 to 2.57:1. In some embodiments, citrulline and taurine together constitute at least 20%, 30%, 40%, 50%, 55%, 60%, 70%, 80% or 90% w/w of the solid composition or solid portion of the composition. In some embodiments, the composition is a solid composition.

In some embodiment, the solid composition does not include more than 30%, or 20% w/w of the combination of any other amino acid, vitamins. peptides, proteins, herb extracts, fatty acids, fibers, probiotics, glucosamine, chondroitin, and CoQ10. In some embodiments, the solid composition does not include more than 10% or 5% w/w malate. In some embodiments, the solid composition does not include more than 10% or 5% w/w arginine. In some embodiments, the solid composition does not include more than 30% of 20% w/w of the combination of arginine, malate, niacin, agmatine, alanine, gamma-aminobutyric acid (GABA), creatine, and dextrin.

In some embodiments, the solid composition does not include more than 10% or 5% why of any other nutritional supplement or activity-enhancing supplement. In some embodiments, the solid composition does not include more than 1% w/w of any other nutritional supplement or activity-enhancing supplement.

In some embodiments, the solid composition further comprises caffeine. In some embodiments, the solid composition further comprises a mineral. In some embodiments, the mineral is selected from calcium, potassium, magnesium, iron, zinc, copper, chromium, selenium, molybdenum, cobalt, nickel, vanadium, tin, strontium, or rubidium.

In some embodiments, the citrulline and the taurine have a weight ratio of 4:1 to 2.85:1. In some embodiments, the citrulline and the taurine have a weight ratio of 3.55:1 to 3:1. In some embodiments, the citrulline and the taurine have a weight ratio of 3.35:1 to 3.08:1. In some embodiments, the citrulline and the taurine have a weight ratio of about 3.17:1.

In some embodiments, the citrulline and the taurine together constitute at least 60% w/w of the solid composition. In some embodiments, the citrulline and the taurine together constitute at least 75% w/w of the solid composition.

In some embodiments, the solid composition further comprises a sweetener, a stabilizer, a binder, a coloring agent, and/or an anticaking agent.

In some embodiments, provided is a drink obtainable by dissolving the solid composition of the present disclosure in water or an aqueous solution.

Also provided, in some embodiments, are methods of using the compositions for improving the athletic performance of a mammalian subject. Also provided, in some embodiments, are methods of using the compositions for or treating or preventing prehypertension, hypertension, or erectile dysfunction (ED).

BRIEF DESCRIPTION OF THE DRAWINGS

The drawings described herein are for illustration purposes only. The drawings are not intended to limit the scope of the present disclosure.

Figure 1:
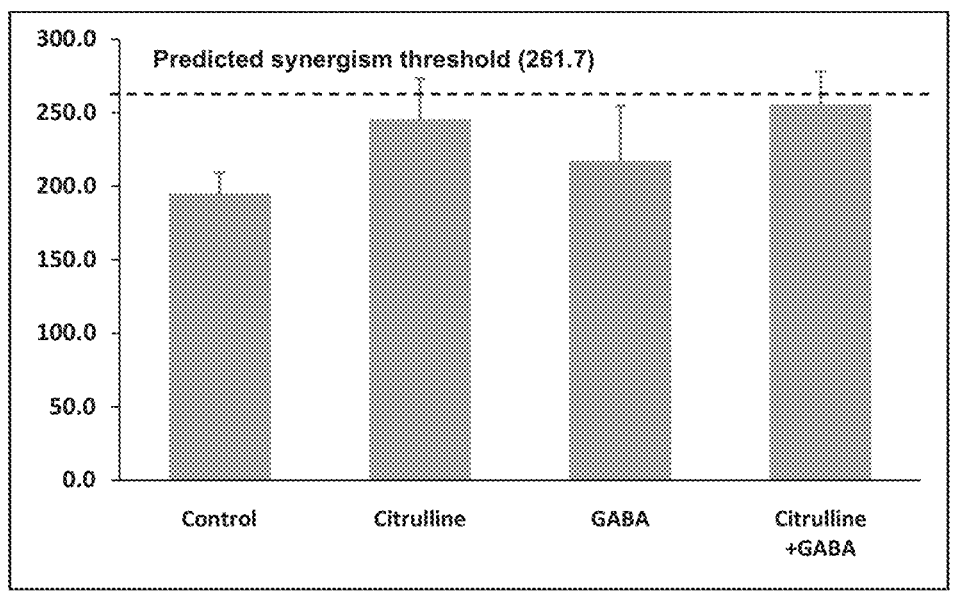
FIG. 1 shows a lack of synergistic effect between citrulline and gamma-aminobutyric acid (GABA) on exercise time to exhaustion. Mice were given either normal saline (control), citrulline (200 mg/kg body weight), or GABA (150 mg/kg body weight), or citrulline/taurine mixture (200 mg/kg+150 mg/kg) 1 hour prior to the test. The mice swam with weights attached to their tails, corresponding to ⅛ of their body weight, and the swimming time to exhaustion were recorded. Values represent means±SE.

Reference is now made in detail to certain embodiments of the present disclosure. While certain embodiments of the present disclosure are described, it will be understood that it is not intended to limit the embodiments of the present disclosure to the disclosed embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

The following description sets forth exemplary embodiments of the present technology. It should be recognized, however, that such description is not intended as a limitation on the scope of the present disclosure but is instead provided as a description of exemplary embodiments.

The potential ability of citrulline to boost endurance performance was assessed with a loaded swimming test in mice. Mice administered with 200 mg/kg citrulline exhibited an increase of about 26% in endurance time on average (from about 194.7 seconds in control to about 245.4 seconds). Another commonly used athletic supplement, gamma-aminobutyric acid (GABA), was able to increase the endurance time too, but at a more modest rate of 11.4%.

The addition of GABA to citrulline resulted in a slightly higher effect than citrulline alone (31% vs. 26%). This slight increase suggests no benefit of the combination given the small benefit based on the almost doubled dosage (350 mg/kg vs. 200 mg/kg).

Surprisingly, when citrulline (200 mg/kg) and taurine (200 mg/kg) were used together, the combinatory effect almost tripled each agent alone (63.1% in combination vs. 15.6% for citrulline and 23.6% for taurine alone). This is clear indication of synergism, which is surprising and unexpected on its own, and more so because of the lack of synergism between citrulline and GABA. Moreover, the magnitude of the synergism (63.1% observed vs. a 35.5% theoretical synergism threshold) is even more surprising.

At a greatly reduced dose of 25 mg/kg, the effect of taurine alone was less pronounced (181 seconds as compared to 168.3 seconds in controls, a mere 7.5% increase). The effect of citrulline, at 75 mg/kg, was also less significant (207.7 seconds). Here, the increases by citrulline and taurine were 23.4% and 7.5%, respectively. The combination treatment, however, resulted in a 53.7% increase, which further underscores the synergism between these two amino acids.

Taurine, however, has an unpleasant astringent bitter taste in a solution. The addition of taurine to citrulline, therefore, may not be a welcome change, even though citrulline itself has a sense of unnatural sweetness. In another surprising discovery of the present disclosure, an aqueous solution of citrulline and taurine in a weight ratio of about 2.5:1 to about 4.5:1, in particular at about 3.17:1, has the best taste. More strikingly, the taste of the mixture at the suitable ratio is better than each of citrulline and taurine alone. In other words, citrulline and taurine can neutralize each other's unpleasant flavor, and this was entirely unexpected.

In accordance within one embodiment of the present disclosure, therefore, provided is a solid composition comprising citrulline and taurine. In some embodiments, a solution that contains the solid composition dissolved in the solution is also provided. Methods of preparing the solid composition or the solution are also provided, in various embodiments.

In some embodiments, the citrulline and the taurine have a weight ratio from about 5:1 to about 1:5. In some embodiments, the weight ratio between citrulline and the taurine is from about 5:1, 4.5:1, 4:1, 3.5:1, 3:1, 2.5:1, 2:1 1.5:1, 1:1, 0.9:1, 0.8:1, 0.7:1, 0.6:1, 0.5:1, 0.4:1, 0.3:1, 0.25:1, or 0.2:1 to about 1:5, 1:4.5, 1:4, 1:3.5, 1:3, 1:2.5, 1:2, 1:1.5, 1:1, 1:0.9, 1:0.8, 1:07, 1:0.6, 1:0.5, 1:0.4, 1:0.3 or 1:02.

In some embodiments, the citrulline and the taurine have a weight ratio of about 4.56:1 to about 2.57:1. In some embodiments, the citrulline and the taurine have a weight ratio of about 4:1 to about 2.85:1. In some embodiments, the citrulline and the taurine have a weight ratio of about 3.55:1 to about 3:1. In some embodiments, the citrulline and the taurine have a weight ratio of about 3.35:1 to about 3.08. In some embodiments, the citrulline and the taurine have a weight ratio of about 3.17.

In some embodiments, the citrulline and the taurine have the weight percentages or weight ratios as shown in Table 1.

TABLE 1

Preferred Taurine % or Citrulline/Taurine Ratios

|  | Weight % of taurine in total | | Weight Ratio (citrulline/taurine) | |
| --- | --- | --- | --- | --- |
|  | low | high | low | high |
| Preferred | 18 | 28 | 4.56 | 2.57 |
| More Preferred | 20 | 26 | 4.00 | 2.85 |
| Evert More Preferred | 22 | 25 | 3.55 | 3.00 |
| Most Preferred | 23 | 24.5 | 3.35 | 3.08 |

In some embodiments, the citrulline and the taurine in combination constitute the substantial portion of the solid composition. In some embodiments, the citrulline and the taurine in combination constitute at least about 20%, 30%, 40%, 50%, 60%, 70%, 75%, 80%, 85%, 90%, 95%, 98%, or 99% of the solid composition.

In some embodiments, the composition does not include a significant portion of other commonly used nutritional or parametrical active agents. Examples of nutritional or parametrical active agents include other amino acids, vitamins, peptides, proteins, herb extracts, fatty acids, fibers, probiotics, glucosamine, chondroitin, and CoQ10. In some embodiments, the composition contains less than about 40%, 35%, 30%, 25%, 20%, 15%, 10%, 9%, 8%, 7%, 6%, 5%, 4%, 3%, 2% or 1% (w/w) of other nutritional or parametrical active agents. In some embodiments, the composition contains less than about 40%, 35%, 30%, 25%, 20%, 15%, 10%, 9%, 8%, 7%, 6%, 5%, 4%, 3%, 2% or 1% (w/w) of other amino acids.

In some embodiments, the composition contains less than about 40%, 35%, 30%, 25%, 20%, 15%, 10%, 9% 8%, 70% 6%, 50% 4%, 3%, 2% or 1% (w/w) malate. In some embodiments, the composition contains less than about 40%, 35%, 30%, 25%, 20%, 15%, 10%, 9%, 8%, 7%, 6%, 5%, 4%, 3%, 2% or 1% (w/w) arginine. In some embodiments, the composition contains less than about 40%, 35%6, 30%, 25%, 20%, 15%, 10%, 9%, 8%, 7%, 6%, 5%, 4%, 3%, 2% or 1% (w/w) the combination of arginine, malate, niacin, agmatine, alanineand dextrin. In some embodiments, the composition contains less than about 40%, 35%, 30%, 25%, 20%, 15/%, 10%, 9%, 8%, 7%, 6%, 5%, 4%, 3%, 2% or 1% (w/w) creatine.

In some embodiments, the composition contains less than about 40%, 35%, 30%, 25%, 20%, 15%, 10%, 9%, 8%, 7%, 6%, 5%, 4%, 3%, 2% or 1% (w/w) other activity/performance-enhancing supplements.

The composition can further include one or more other excipients or ingredients. Non-limiting examples of excipients include diluents, disintegrants, binders, lubricants, sweeteners, flavoring agents and anti-cake agents.

Diluents act as fillers in nutraceutical/pharmaceutical tablets to increase weight and improve content uniformity. Examples include, without limitation, microcrystalline cellulose, powdered cellulose, pregelatinized starch, starch, lactitol, mannitol, sorbitol, maltodextrin and combinations thereof.

Disintegrants are agents added to solid formulations (e.g., tablets) to promote the breakup of the tablet (or capsule "slugs") into smaller fragments in an aqueous environment thereby increasing the available surface area and promoting a more rapid release of the drug substance. Examples include, without limitation, croscarmellose sodium, crospovidone, starch, sodium carboxymethyl starch, low-substituted hydroxypropyl cellulose and combinations thereof.

Binders are formulated to act as an adhesive to bind together powders, granules and other dry ingredients to impart to the product the necessary mechanical strength. Examples include, without limitation, distilled water, ethanol, hypromellose, sodium carboxymethylcellulose, povidone, ethyl cellulose and combinations thereof.

Lubricants are agents added to tablet and capsule formulations to improve the powder processing properties of the formulation. Lubricants (glidants) can enhance the powder flow by reducing the inter-particle friction. Non-limiting examples include sodium stearyl fumarate, magnesium stearate, calcium stearate, stearic acid, glyceryl behenate, and combinations thereof.

Non-limiting examples of sweeteners include xylitol, sorbitol, mannitol, maltitol, lactitol, isomalt, erythritol, aspartame, acesulfame potassium, alitame, sodium saccharin, three Sucralose, neotame, cyclamate, and combinations thereof.

Non-limiting examples of flavoring agents include orange flavor, orange flavor, mango flavor, peach flavor, grapefruit flavor, and combinations thereof.

Anti-caking agents are additives placed in powdered or granulated materials, such as table salt, to prevent the formation of lumps and for casing packaging, transport, and consumption. Anticaking agents function either by adsorbing excess moisture, or by coating particles and making them water repellent. Non-limiting examples of anti-caking agents include silica, tricalcium phosphate, microcrystalline cellulose and combination thereof.

In addition, in effervescent tablet or granules, an agent that produces carbon dioxide is needed, and their examples include acidic materials such as citric acid, tartaric acid, fumaric acid, malic acid, adipic acid, succinic acid, ascorbic acid, maleic acid, and combinations thereof. Further included in the effervescent agent are alkali metal hydrogencarbonates including sodium hydrogencarbonate, potassium hydrogencarbonate, and combinations thereof.

In some embodiments, the composition further includes caffeine. In some embodiments, the composition further includes a mineral, such as calcium, potassium, magnesium, iron, zinc, copper, chromium, selenium, molybdenum, cobalt, nickel, vanadium, tin, strontium, or rubidium.

The solid compositions of the present disclosure can be provided as tablets, capsules, powders, granules, or effervescent tablets or granules. Solutions (e.g., beverages) that include citrulline and the taurine are also provided.

The solutions can be prepared by dissolving a solid composition of the present disclosure in water or an aqueous solution. In some embodiments, the solution includes from about 0.1% (w/w) to about 20% (w/w) of a combination of citrulline and the taurine. In some embodiments, the solution includes at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (w/w) of the combination of citrulline and the taurine. In some embodiments, the solution includes no more than about 20%, 18%, 15%, 12%, 10%, 9%, 8%, 7%, 6%, 5%, 4%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, or 1% of the combination of citrulline and the taurine.

In some embodiments, the solution has a pH of about 2.0 to about 9.0. In some embodiments, the solution has a pH of at least about 2.0, 2.5, 3.0, 3.5, 4, 4.5, 5, 5.5, 6, 6.5, or 7. In some embodiments, the solution has a pH of not higher than about 9, 8.5, 8, 7.5, 7, 6.5, 6, 5.5, 5, 4.5 or 4. In some embodiments, the pH is from about 2.5 to about 3.5. In some embodiments, the pH is from about 3 to 4. In some embodiments, the pH is from about 3.5 to 4.5. In some embodiments, the pH is from about 4 to 5. In some embodiments, the pH is from about 5 to 6. In some embodiments, the pH is from about 6 to 7. In some embodiments, the pH is from about 7 to 8. In some embodiments, the pH is from about 8 to 9.

In some embodiments, the citrulline and the taurine in the solution have a weight ratio of about 4.56:1 to about 2.57:1. In some embodiments, the citrulline and the taurine in the solution have a weight ratio of about 4:1 to about 2.85:1. In some embodiments, the citrulline and the taurine in the solution have a weight ratio of about 3.55:1 to about 3:1. In some embodiments, the citrulline and the taurine in the solution have a weight ratio of about 3.35:1 to about 3.08. In some embodiments, the citrulline and the taurine in the solution have a weight ratio of about 3.17.

Specific examples of solid compositions and solutions disclosed here include, without limitation, those provided in Experimental Example 5.

Methods for preparing and using the aqueous solutions of the present disclosure are also provided. In some embodiments, the solutions can be prepared by adding each of the ingredients into a water-based solution.

In various embodiments, the solid compositions and solutions disclosed herein can be used in methods for enhancing stamina, athletic performance, endurance, and/or reducing muscle soreness, fatigue or cramping in a subject in need thereof. In some embodiments, the solid compositions and solutions disclosed herein can be used in methods for preventing or treating hypertension or prehypertension in a subject in need thereof. In some embodiments, the solid compositions and solutions disclosed herein can be used in methods for preventing or treating erectile dysfunction (ED) in a male subject in need thereof. The method, in some embodiments, entailsorally administering to the subject an effective amount of the solid composition or solution of the present disclosure.

In some embodiments, provided is a method or use for improving the athletic performance of a mammalian subject. In some embodiments, provided is a method or use for enhancing the physical endurance or reducing fatigue of a mammalian subject. In some embodiments, provided is a method or use for enhancing the muscular strength of a mammalian subject.

In some embodiments, provided is a method or use for treating or preventing erectile dysfunction (ED) in a male mammalian subject. In some embodiments, wherein the ED is mild or moderate. In some embodiments, provided is a method or use for treating or preventing hypertension or prehypertension in a mammalian subject.

In various embodiments, the method entails administering, in particular orally, to the subject a solid composition or a drink of the disclosure. In some embodiments, about 0.1 g to about 100 g of the combination of citrulline and the taurine are administered daily. In some embodiments, the daily dose of the combination of citrulline and the taurine is at least 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 8 g, 8 g, 9 g, 10 g, 15 g, 20 g, 30 g, 40 g, or 50 g. In some embodiments, the daily dose of the combination of citrulline and the taurine is not greater than 100 g, 90 g, 80 g, 70 g, 60 g, 50 g, 40 g, 30 g, 20 g, 15 g, 10 g, 9 g, 8 g, 7 g, 6 g, 5 g, 4 g, 3 g, 2 g or 1 g.

In some embodiments, the solid composition or the drink is administered once, twice or three times daily. In some embodiments, the solid composition or the drink is administered prior to, during, or following physical activities, or prior to a sexual activity.

In some embodiments, the administration follows an intense physical activity by the subject. In one embodiment, the administration is made before an intense physical activity by the subject.

In some embodiments, the effective amount of the solution is about 30 ml, 50 ml, 75 ml, 100 ml, 120 ml, 150 ml, 200 ml, 250 ml, 300 ml, 400 ml, or 500 ml, without limitation. In some embodiments, the effective amount of the solid composition is about 0.1, 0.2, 0.5 g, 1 g, 1.5 g, 2 g, 3 g, 4 g, 5 g, 10 g, 15 g or 20 g without limitation.

In some embodiments, the subject experiences muscle soreness, fatigue, or cramping. In some embodiments, the subject, following the administration, experiences reduced muscle soreness, fatigue or cramping. In some embodiment, the subject desires the flavor of the solution.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1. Effects of Citrulline and GABA on Endurance and Muscle Strength

This example tested the effect of citrulline on the endurance and muscle strength of mice in exercise, and explores the potential synergistic effect of gamma-aminobutyric acid (GABA) to citrulline.

Materials and Methods

Animals.

Adult (8-10 weeks) male ICR mice were used in this study and purchased from Beijing Vital River Laboratory Animal Technology Co., Ltd. All the mice were provided with a normal diet and water ad libitum. All procedures were approved by institutional guidelines and the Animal Care and Use Committee (Huazhong University of Science and Technology, Wuhan, China) of the university's animal core facility. The mice were group-housed under a 12 h light-dark cycle (lights on at 8:00 a.m.), at consistent humidity (50±5%), and ambient temperature (22~24° C.).

The animals were bred with three mice per cage in the laboratory, and were acclimatized for 1 week before the experiments. The mice were grouped randomly for each experiment. The mice in each group were given the corresponding dose amino acid and the control group was treated with the equal volume of normal saline (NS) through intragastric administration. Loaded swimming experiments were performed to assess the acute effect of the amino acids on endurance one hour after the treatment The NS injection were purchased from Beijing Pharmaceutical Group Co., Ltd. The amino acid powders were dissolved in NS and then were intragastric administration to mice by lavage needle (Beijing Vital River Laboratory Animal Technology Co., Ltd.).

Loaded Swimming Test

Acute effects on endurance performance were assessed by loaded swimming test one hour after the amino acid treatment. The swimming exercise was carried out in a tank (diameter 120 cm) filled with fresh water to 30-cm depth at 24±2° C. A tin wire (⅛ of body weight) was attached on the tail of the mouse. Each mouse was considered to have reached exhaustion when it failed to rise its face to the surface of the water for inhale within 5 s period. The length of time each mouse kept swimming before exhaustion (exercise time to exhaustion) was recorded. At the end of the session, the mice were removed from the water, dried with paper towels, and placed back in their home cages.

Results

Sixty mice were randomly divided into four groups (n=15 per group). Each of the four group were treated with NS, citrulline (200 mg/kg body weight), GABA (150 mg/kg body weight), and citrulline/GABA mixture (200 mg/kg+150 mg/kg) respectively. The results were summarized below (Table 2 and FIG. 1).

TABLE 2

Effects of citrulline and citrulline/GABA combination on exercise time to exhaustion

|  | Control | Citrulline | GABA | Citrulline + GABA |
| --- | --- | --- | --- | --- |
| Average Time (s) | 194.7 | 245.4 | 216.8 | 255 |
| SE | 14.67 | 28.01 | 37.88 | 23.03 |
| Increase | — | 26% | 11.4% | 31% |

Citrulline increased the endurance time, as compared to vehicle control, by about 26%. GABA alone also increased the endurance, though at a slightly lower rate, at about 11.4%. The combination of citrulline and GABA resulted in a 31% increase.

A commonly accepted way to estimate the combinatory effect, without synergism, is Ec=Ea+Eb−Ea*Eb, where Ea, Eb and Ec represent the effects of agents a and b and their combination, respectively. Here, the estimated combinatory effect without synergism would be a 34.4% increase (vs. a sum of both values being 37.4%). In FIG. 1, the predicted synergism threshold (261.7 seconds) is indicated as a horizontal dotted line. The observed combinatory effect was an endurance enhancement of 31% (255 seconds), suggesting that there was no synergism between citrulline and GABA. Also, given the modest added effect of GABA (5% over citrulline's 26%) from the 150 mg/kg dose, GABA does not appear to be promising additive to citrulline.

This result was disappointing as GABA was suggested to have the ability to enhance muscle building. Further, according to Shyamaladevi et al., *Brain Research Bulletin* 57(2): 231-6 (2002), for instance, nitric oxide (NO) increases the blood-brain barrier permeability for GABA. Meanwhile, citrulline boosts NO production in the body. Therefore, when citrulline is supplied to the body, it would have been expected to raise the availability of GABA in the brain. The interaction between the two agents, therefore, would have been expected to exhibit synergy. Such synergy, however, was not observed.

Example 2. Unexpected Synergy Between Citrulline and Taurine on Endurance and Muscle Strength This example continued to look for agents that could significantly further increase citrulline's activity in enhancing the endurance and muscle strength of mice in exercise. Taurine was surprisingly found to have such synergism with citrulline.

The methods used here are the same as in Example 1, but GABA (150 mg/kg) was replaced by taurine (200 mg/kg). The results were summarized below (Table 3 and FIG. 2).

TABLE 3

Effect of citrulline taurine combination on exercise time to exhaustion

|  | Control | Citrulline | Taurine | Citrulline + Taurine |
|---|---|---|---|---|
| Average Time (s) | 168.3 | 194.6 | 208 | 274.5 |
| SE | 12.58 | 17.02 | 22.20 | 20.33 |
| Increase | — | 15.6% | 23.6% | 63.1% |

Figure 2:
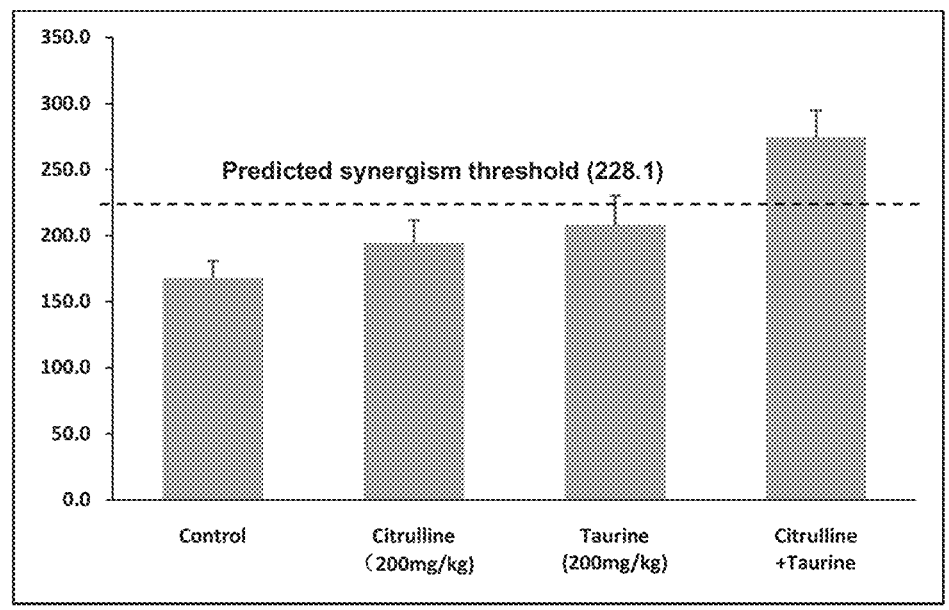
FIG. 2 shows the synergistic effect of citrulline and taurine on exercise time to exhaustion. Mice were given either normal saline (control), citrulline (200 mg/kg body weight), or taurine (200 mg/kg body weight), or citrulline/taurine mixture (200 mg/kg+200 mg/kg) 1 hour prior to the test. The mice swam with weights attached to their tails, corresponding to ⅛ of their body weight, and the swimming time to exhaustion were recorded. Values represent means±SE.

Citrulline and taurine increased the endurance time by 15.6% and 23.6%, respectively. As the synergism estimation methodology explained in Example 1, the estimated combinatory effect without synergism would be a 35.5% increase (vs. a sum of both values being 39.2%). In FIG. 2, the predicted synergism threshold (228.1 seconds) is indicated as a horizontal dotted line. The observed combinatory effect, however, was an endurance enhancement of 63.1% (274.5 seconds), clearly indicating a strong synergy between these two amino acids.

Example 3. Synergy between Lower Doses of Citrulline and Taurine on Endurance and Muscle Strength This example tested whether the synergism between citrulline and taurine is still present in lower doses, and confirmed the synergism.

The methods used here are the same as in Example 1. Sixty mice were randomly divided into four groups (n=15 per group). Each of the four group were treated with NS, citrulline (75 mg/kg body weight), taurine (25 mg/kg body weight), and citrulline taurine mixture (75 mg/kg+25 mg/kg) respectively. The results were summarized below (Table 4 and FIG. 3).

TABLE 4

Effect of lower doses of citrulline taurine combination on exercise time to exhaustion.

|  | Control | Citrulline | Taurine | Citrulline + Taurine |
|---|---|---|---|---|
| Average Time (s) | 168.3 | 207.7 | 181 | 258.7 |
| SE | 18.53 | 16.67 | 16.56 | 22.05 |
| Increase | — | 23.4% | 7.5% | 53.7% |

Figure 3:
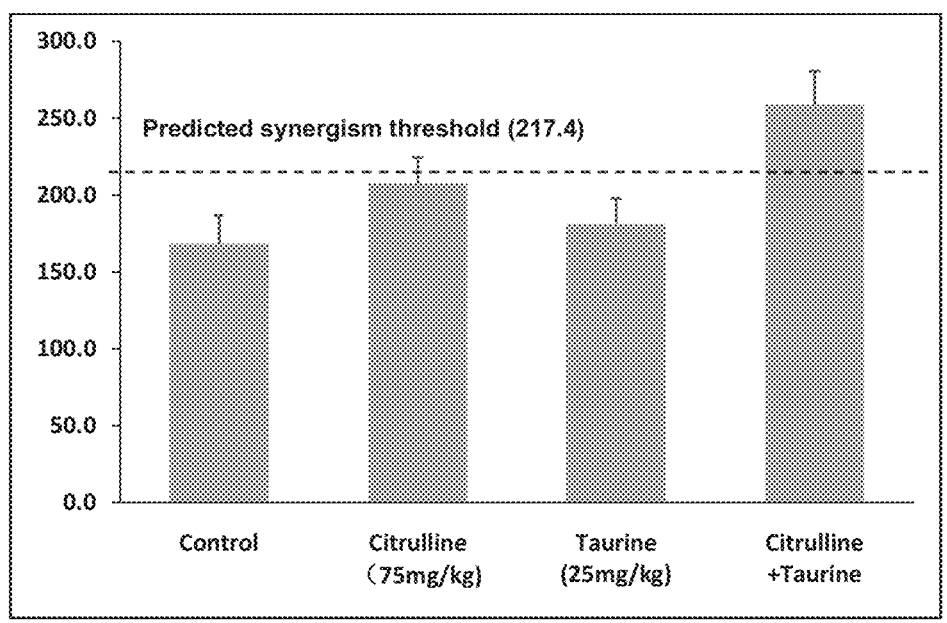
FIG. 3 shows the synergistic effect of citrulline and taurine, on lower doses, on exercise time to exhaustion. Mice were given either normal saline (control), or citrulline (75 mg/kg body weight), or taurine (25 mg/kg body weight), or citrulline taurine mixture (75 mg/kg+25 mg/kg) 1 hour prior to the test. The mice swam with weights attached to their tails, corresponding to ⅛ of their body weight, and the swimming time to exhaustion were recorded. Values represent means±SE.

Here, the lower doses of citrulline and taurine increased the endurance time by 23.4% and 7.5%, respectively. The estimated combinatory effect without synergism would be a 29.1% increase (vs. a sum of both values being 30.9%). In FIG. 3, the predicted synergism threshold (217.4 seconds) is indicated as a horizontal dotted line. The observed combinatory effect, however, was an endurance enhancement of 53.7% (258.7 seconds), again a showing of strong synergy between these two amino acid seven at the lowered doses.

Further, Examples 2 and 3 demonstrate that the synergism between citrulline and taurine exist at different dose levels and at different ratios (e.g., 1:1 and 3:1).

Example 4. Taste Surveys

Citrulline solution does not have a strong taste, but has a sense of unnatural sweetness that is distinguishable. The taurine solution, however, clearly has an astringent bitter taste, even at a fairly diluted concentration. The mixture of citrulline and taurine, therefore, presents a challenge in terms of flavoring, as compared to citrulline alone. This example explored options to minimize the unpleasant taste with different ratios of these two amino acids.

Taste Survey No. 1
Method

Six different citrulline-taurine mixtures were prepared with citrulline/taurine ratios ranging from 8/0, 7/1, 4/1, 6/2, 5/3, to 4/4. Testing samples were prepared by dissolving 6 grams of each mixture in 250 ml drinking water separately. Thirty volunteers, 12 females and 18 males, aged from 22-55 participated in the test. The volunteers were asked to taste each sample without knowing the composition of the samples. Each volunteer sorted the samples from 1 to 6, with 1 being the most liked and 5 being the least liked sample.

Results

The survey results are shown in Table 5.

TABLE 5

Survey results

| | Citrulline:Taurine Ratio | | | | | |
|---|---|---|---|---|---|---|
| Indvidual | 8:0 | 7:1 | 4:1 | 6:2 | 5:3 | 4:4 |
| P01 | 6 | 5 | 4 | 3 | 1 | 2 |
| P02 | 4 | 3 | 2 | 1 | 6 | 5 |
| P03 | 4 | 3 | 1 | 2 | 5 | 6 |
| P04 | 6 | 3 | 2 | 1 | 4 | 5 |
| P05 | 4 | 3 | 1 | 2 | 5 | 6 |
| P06 | 5 | 2 | 3 | 1 | 4 | 6 |

TABLE 5-continued

Survey results

| | Citrulline:Taurine Ratio | | | | | |
| --- | --- | --- | --- | --- | --- | --- |
| Indvidual | 8:0 | 7:1 | 4:1 | 6:2 | 5:3 | 4:4 |
| P07 | 6 | 4 | 3 | 1 | 2 | 5 |
| P08 | 5 | 6 | 4 | 2 | 1 | 3 |
| P09 | 4 | 3 | 2 | 1 | 5 | 6 |
| P10 | 5 | 3 | 2 | 1 | 4 | 6 |
| P11 | 3 | 4 | 5 | 1 | 2 | 6 |
| P12 | 6 | 4 | 2 | 1 | 3 | 5 |
| P13 | 4 | 3 | 2 | 1 | 6 | 5 |
| P14 | 2 | 3 | 4 | 1 | 5 | 6 |
| P15 | 4 | 2 | 1 | 3 | 6 | 5 |
| P16 | 6 | 5 | 3 | 1 | 2 | 4 |
| P17 | 3 | 4 | 2 | 1 | 5 | 6 |
| P18 | 6 | 4 | 5 | 3 | 1 | 2 |
| P19 | 4 | 2 | 6 | 5 | 3 | 1 |
| P20 | 1 | 3 | 5 | 6 | 2 | 4 |
| P21 | 3 | 4 | 2 | 5 | 1 | 6 |
| P22 | 6 | 3 | 1 | 2 | 4 | 5 |
| P23 | 4 | 3 | 1 | 2 | 6 | 5 |
| P24 | 2 | 4 | 3 | 1 | 5 | 6 |
| P25 | 4 | 1 | 3 | 2 | 6 | 5 |
| P26 | 5 | 4 | 1 | 2 | 3 | 6 |
| P27 | 4 | 3 | 1 | 2 | 5 | 6 |
| P28 | 4 | 1 | 3 | 5 | 2 | 6 |
| P29 | 4 | 3 | 1 | 2 | 5 | 6 |
| Total | 124 | 95 | 75 | 61 | 109 | 145 |

Figure 4:
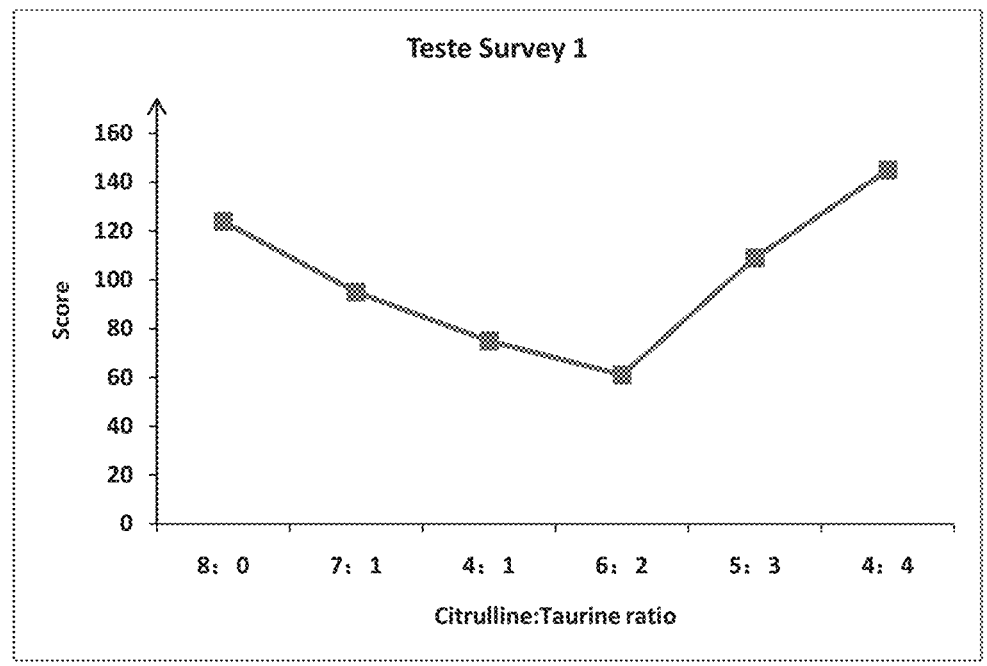
FIG. 4 charts the results of a taste survey of various drinks having different ratios of citrulline and taurine.

The results are plotted in FIG. 4, which indicates that when citrulline and taurine were mixed at about a 3:1 weight ratio, the taste was the most favorable. What was entirely unexpected and even striking is that the mixtures had more favorable tastes than each of its ingredients alone. For instance, citrulline alone (i.e., 8:0 citrulline to taurine) had a taste survey score of 124. When taurine was added, the taste survey score improved to 95 (7:1), 75 (4:1) and 61 (6:2) and then deteriorated when more taurine was added. In other words, addition of the more unfavorable taurine was able to even reduce the less unfavorable taste of citrulline.

To further investigate the tastes of citrulline taurine combinations, nine different citrulline-taurine mixtures were prepared with taurine content in the mixture of 20%, 22%, 24%, 25%, 26%, 28%, 30%, 32%, and 34%. Testing samples were prepared by dissolving 6 grams of each mixture in 250 ml drinking water separately. Twenty volunteers, 11 females and 9 males, aged from 22-55 participated in the test. The volunteers were asked to taste each sample without knowing the composition of the samples. Each volunteer sorted the samples from 1 to 9, with 1 being the most liked and 5 being the least liked sample. The survey results are provided in Table 6 below.

TABLE 6

Survey results

| | Taurine content in the mixture | | | | | | | | |
| --- | --- | --- | --- | --- | --- | --- | --- | --- | --- |
| Individual | 20% | 22% | 24% | 25% | 26% | 28% | 30% | 32% | 34% |
| Q01 | 8 | 2 | 1 | 6 | 9 | 7 | 5 | 4 | 3 |
| Q02 | 1 | 2 | 3 | 5 | 9 | 4 | 6 | 8 | 7 |
| Q03 | 3 | 2 | 1 | 4 | 6 | 7 | 8 | 9 | 5 |
| Q04 | 9 | 8 | 1 | 7 | 2 | 6 | 4 | 3 | 5 |
| Q05 | 2 | 3 | 1 | 4 | 5 | 7 | 6 | 9 | 8 |
| Q06 | 4 | 3 | 5 | 1 | 2 | 6 | 7 | 9 | 8 |
| Q07 | 4 | 1 | 2 | 3 | 5 | 7 | 6 | 9 | 8 |
| Q08 | 2 | 1 | 4 | 5 | 3 | 6 | 7 | 8 | 9 |
| Q09 | 5 | 4 | 2 | 3 | 1 | 6 | 7 | 8 | 9 |
| Q10 | 5 | 2 | 1 | 3 | 4 | 7 | 6 | 8 | 9 |
| Q11 | 3 | 1 | 2 | 4 | 5 | 6 | 7 | 9 | 8 |
| Q12 | 7 | 6 | 5 | 2 | 9 | 4 | 3 | 1 | 8 |
| Q13 | 3 | 1 | 2 | 4 | 5 | 6 | 7 | 9 | 8 |
| Q14 | 7 | 6 | 5 | 4 | 3 | 2 | 1 | 8 | 9 |
| Q15 | 3 | 1 | 2 | 6 | 5 | 4 | 8 | 7 | 9 |
| Q16 | 4 | 3 | 2 | 1 | 5 | 6 | 7 | 9 | 8 |
| Q17 | 5 | 2 | 3 | 1 | 4 | 7 | 6 | 8 | 9 |
| Q18 | 5 | 4 | 2 | 3 | 1 | 6 | 7 | 8 | 9 |
| Q19 | 3 | 2 | 4 | 1 | 8 | 6 | 9 | 7 | 5 |
| Total | 83 | 54 | 48 | 67 | 91 | 110 | 117 | 141 | 144 |

Figure 5:
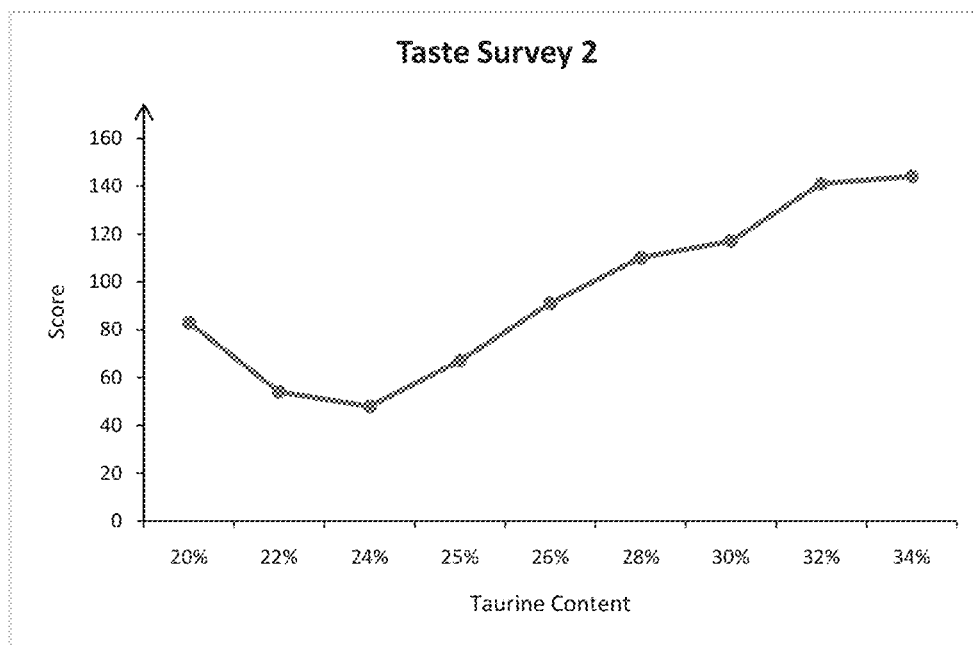
FIG. 5 charts the results of a second taste survey of various drinks having different ratios of citrulline and taurine.

As the composition difference between samples gets smaller, the curve became shallower. However, the result indicates that samples with taurine content between 20% and 28% were best "liked", with 24% being the winner (FIG. 5).

Example 5. Production Samples

This example lists a number of production samples in different forms (solid or in solution).

Production Sample 1 (powder):

| Ingredient | Amount | Unit |
| --- | --- | --- |
| Citrulline | 76 | parts |
| Taurine | 24 | parts |
| Maltodextrin | 1.5 | parts |
| Microcrystalline cellulose | 1 | parts |
| Food flavor | 1 | parts |

Production sample 1 is prepared as follows. The ingredients are weighed according to the formula, and are mixed together in a uniform manner. Alternatively, they are added into water is then spray dried.

Production Sample 2 (oral solution):

| Ingredient | Amount | Unit |
| --- | --- | --- |
| Citrulline | 1.52 | % |
| Taurine | 0.48 | % |
| Creatine monohydrate | 0.15 | % |
| Maltodextrin | 0.1 | % |
| Concentrated lemon juice | 0.005 | % |
| Sodium cyclamate | 0.0034 | % |
| Acesulfame | 0.00255 | % |
| Sodium bicarbonate | 0.001 | % |
| Aspartame | 0.00085 | % |
| Orange flavor | 0.0005 | % |
| Water | q.s. to 100 mg | % |

Production sample 2 is prepared as follows. The ingredients are weighed according to the formula, stirred and dissolved uniformly to obtain a mixed liquid. The mixture is filtered and then bottled. Sterilization is carried out to obtain a finished product.

| Production Sample 3 (tablets or granules): | | |
| --- | --- | --- |
| Ingredient | Amount | Unit |
| Citrulline | 80 | parts |
| Taurine | 20 | parts |
| Filler | 25 | parts |
| Disintegrant | 2.5 | parts |
| Lubricant | 2.5 | parts |
| Binder | 2.5 | parts |
| Sweetener | 0.1 | parts |

Production sample 3 is prepared as follows. The ingredients are weighed according to the formula and are mixed with water in a wet granulator. The particles are then dried in an oven to obtain granules. The granules can be pressed to prepare tablets.

| Production Sample 4 (effervescent granules): | | |
| --- | --- | --- |
| Ingredient | Amount | Unit |
| Citrulline | 66 | parts |
| Taurine | 33 | parts |
| Filler | 25 | parts |
| Citric acid | 25 | parts |
| Sodium bicarbonate | 25 | parts |

Production sample 4 is prepared as follows. The ingredients are weighed according to the formula and are mixed with water in a wet granulator. The particles are then dried in an oven to obtain effervescent granules.

| Production Sample 5 (effervescent tablets): | | |
| --- | --- | --- |
| Ingredient | Amount | Unit |
| Citrulline | 75 | parts |
| Taurine | 25 | parts |
| Filler | 25 | parts |
| Disintegrant | 5 | parts |
| Lubricant | 5 | parts |
| Sweetener | 2.5 | parts |
| Citric acid | 25 | parts |
| Sodium bicarbonate | 25 | parts |

Production sample 5 is prepared as follows. The ingredients (except citric acid and sodium bicarbonate) are weighed according to the formula and are mixed with water in a wet granulator. The particles are then dried in an oven. Citric acid and sodium bicarbonate are then added to the particles and pressed to prepare effervescent tablets.

| Production Sample 6 (capsules): | | |
| --- | --- | --- |
| Ingredient | Amount | Unit |
| Citrulline | 76 | parts |
| Taurine | 24 | parts |
| Filler | 25 | parts |
| Disintegrant | 5 | parts |
| Lubricant | 5 | parts |
| Binder | 5 | parts |

Production sample 6 is prepared as follows. The ingredients (except citric acid and sodium bicarbonate) are weighed according to the formula and are mixed with water in a wet granulator. The particles are then dried in an oven and filled into capsules in a filling machine.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A solid composition comprising citrulline and taurine, wherein the citrulline and the taurine have a weight ratio of 5:1 to 1:1 and together constitute at least 75% w/w of the solid composition.

2. The solid composition of claim 1, wherein the citrulline and the taurine have a weight ratio of 4.56:1 to 2.57:1.

3. The solid composition of claim 2, which does not include more than 20%, w/w of the combination of any other amino acid, vitamins, peptides, proteins, herb extracts, fatty acids, fibers, probiotics, glucosamine, chondroitin, and CoQ10.

4. The solid composition of claim 3, which does not include more than 5% w/w malate.

5. The solid composition of claim 3, which does not include more than 5% w/w arginine.

6. The solid composition of claim 1, which does not include more than 20% w/w of the combination of arginine, malate, niacin, agmatine, alanine, gammaaminobutyric acid (GABA), creatine, and dextrin.

7. The solid composition of claim 1, further comprising caffeine.

8. The solid composition of claim 1, further comprising a mineral.

9. The solid composition of claim 8, wherein the mineral is selected from calcium, potassium, magnesium, iron, zinc, copper, chromium, selenium, molybdenum, cobalt, nickel, vanadium, tin, strontium, or rubidium.

10. The solid composition of claim 1, wherein the citrulline and the taurine have a weight ratio of 4:1 to 2.85:1.

11. The solid composition of claim 10, wherein the citrulline and the taurine have a weight ratio of 3.55:1 to 3:1.

12. The solid composition of claim 10, wherein the citrulline and the taurine have a weight ratio of 3.35:1 to 3.08:1.

13. The solid composition of claim 10, wherein the citrulline and the taurine have a weight ratio of about 3.17:1.

14. The solid composition of claim 1, wherein the citrulline and the taurine together constitute at least 80% w/w of the solid composition.

15. The solid composition of claim 14, wherein the citrulline and the taurine together constitute at least 85% w/w of the solid composition.

16. A drink obtainable by dissolving the solid composition of claim 1 in water or an aqueous solution.

17. A method for improving the athletic performance of a mammalian subject, comprising orally administering to the subject the solid composition of claim 1.

18. A method for treating hypertension or prehypertension in a mammalian subject, comprising orally administering to the subject the solid composition of claim 1.

* * * * *